(12) United States Patent
Lee et al.

(10) Patent No.: US 9,605,304 B2
(45) Date of Patent: Mar. 28, 2017

(54) ULTRA-STABLE OLIGONUCLEOTIDE-GOLD AND-SILVER NANOPARTICLE CONJUGATES AND METHOD OF THEIR PREPARATION

(75) Inventors: Thomas Ming Hung Lee, Hong Kong (CN); Kwun Fung Wong, Hong Kong (CN); Shea Ping Yip, Hong Kong (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 1343 days.

(21) Appl. No.: 13/437,940

(22) Filed: Apr. 3, 2012

(65) Prior Publication Data

US 2013/0022682 A1 Jan. 24, 2013

Related U.S. Application Data

(60) Provisional application No. 61/510,056, filed on Jul. 20, 2011.

(51) Int. Cl.
 *C12Q 1/68* (2006.01)
 *B82Y 5/00* (2011.01)
 *B82Y 15/00* (2011.01)

(52) U.S. Cl.
 CPC ........... *C12Q 1/6844* (2013.01); *B82Y 5/00* (2013.01); *B82Y 15/00* (2013.01)

(58) Field of Classification Search
 None
 See application file for complete search history.

(56) References Cited

U.S. PATENT DOCUMENTS

| | | |
|---|---|---|
| 6,548,168 B1 | 4/2003 | Mulvaney |
| 8,470,442 B2 * | 6/2013 | Lee ............... B22F 1/0018 427/200 |
| 2002/0127574 A1 * | 9/2002 | Mirkin .............. B82Y 15/00 435/6.12 |
| 2003/0148282 A1 | 8/2003 | Mirkin |
| 2009/0061010 A1 * | 3/2009 | Zale et al. .............. 424/501 |
| 2010/0234579 A1 | 9/2010 | Mirkin |

OTHER PUBLICATIONS

Jia et al. "In situ preparation of magnetic chitosan/Fe3O4 composite nanoparticles in tiny pools of water-in-oil microemulsion" 2006; Elsevier, Reactive & Functional Polymers, vol. 66, pp. 1552-1558.*
Liu, Yanli et al.; "Synthesis, Stability, and Cellular Internalization of Gold Nanoparticles Containing Mixed Peptide-Poly(ethylene glycol) Monolayers," 2007; ACS, Analytical Chemistry, vol. 79, No. 6.*

(Continued)

*Primary Examiner* — Suzanne Ziska
*Assistant Examiner* — Ivan Greene
(74) *Attorney, Agent, or Firm* — Duane Morris LLP; Siegfried J. W. Ruppert

(57) ABSTRACT

A method for stabilizing conjugates between macromolecule and nanoparticle by forming a thin reinforcement layer over the surface of a nanoparticle after macromolecule chains have attached to the surface of the nanoparticle. The stabilized conjugates can be used in a wide range of applications such as in vitro diagnostics, in vivo imaging and therapeutics, which need to be conducted under various severe or harsh conditions.

24 Claims, 11 Drawing Sheets

5'-HS-(CH2)6-(OCH2CH2)6-GCAATAAACTCAACAGGAGCAG-3'

MPTMS: (3-mercaptopropyl)trimethoxysilane

(56) References Cited

OTHER PUBLICATIONS

Rosi, Nathaniel L. et al.; "Oligonucleotide-Modified Gold Nanoparticles for Intracellular Gene Regulation," 2006, Science, vol. 312, No. 5776, pp. 1027-1023.*

Zhao, Weian et al.; "Design of Gold Nanoparticle-Based Colorimetric Biosensing Assays," 2008, WILEY-VCH; ChemBioChem, vol. 9, No. 15, pp. 2363-2371.*

Liu, Yanli et al.; "Synthesis, Stability, and Cellular Internalization of Gold Nanoparticles Containing Mixed Peptide-Poly(ethylene glycol) Monolayers," 2007; ACS, Analytical Chemistry, vol. 79, No. 6, pp. 2221-2229.*

Buining, Paul A. et al.; "Preparation of Functional Silane-Stabilized Gold Colloids in the (Sub)nanometer Size Range," 1997, American Chemical Society; Langmuir, vol. 13, No. 15, pp. 3921-3926.*

Kraus et al.; "Biphasic Synthesis of Au@SiO2 Core-Shell Particles with Stepwise Ligand Exchange," 2010; ACS, Langmuir, vol. 27, No. 2, pp. 727-732.*

Zhu et al.; "Surface modification and functionalization of semiconductor quantum dots through reactive coating of silanes in toluene," 2007; Royal Society of Chemistry, Journal of Materials Chemistry, vol. 17, pp. 800-805.*

Alivisatos, A. P.; Johnsson, K. P.; Peng, X.; Wilson, T. E.; Loweth, C. J.; Bruchez, M. P.; Schultz, P. G. Organization of 'nanocrystal molecules' using DNA. *Nature* 1996, 382, 609-611.

Demers, L. M.; Mirkin, C. A.; Mucic, R. C.; Reynolds, R. A.; Letsinger, R. L.; Elghanian, R.; Viswanadham, G. A Fluorescence-based method for determining the surface coverage and hybridization efficiency of thiol-capped oligonucleotides bound to gold thin films and nanoparticles. *Anal. Chem.* 2000, 72, 5535-5541.

Dhar, S., Daniel, W. L.; Giljohann, D. A.; Mirkin, C. A.; Lippard, S. J. Polyvalent oligonucleotide gold nanoparticle conjugates as delivery vehicles for platinum(IV) warheads. *J. Am. Chem. Soc.* 2009, 131, 14652-14653.

Dougan, J. A.; Karlsson, C.; Smith, W. E.; Graham, D. Enhanced oligonucleotide—nanoparticle conjugate stability using thioctic acid modified oligonucleotides. *Nucleic Acids Res.* 2007, 35, 3668-3675.

Elghanian, R.; Storhoff, J. J.; Mucic, R. C.; Letsinger, R. L.; Mirkin, C. A. Selective colorimetric detection of polynucleotides based on the distance-dependent optical properties of gold nanoparticles. *Science* 1997, 277, 1078-1081.

Huang, C.-C.; Huang, Y.-F.; Cao, Z.; Tan, W.; Chang, H.-T. Aptamer-modified gold nanoparticles for colorimetric determination of platelet-derived growth factors and their receptors. *Anal. Chem.* 2005, 77, 5735-5741.

Jia, Z., Yujun, W., Yangcheng, L., Jingyu, M., Guangsheng, L. In situ preparation of magnetic chitosan/Fe3O4 composite nanoparticles in tiny pools of water-in-oil microemulsion. *Reactive & Functional Polymers* 2006, 66, 1552-1558.

Jung, Y.L., Jung, C., Parab, H., Li, T., Park, H.G. Direct colorimetric diagnosis of pathogen infections by utilizing thiol-labeled PCR primers and unmodified gold nanoparticles. *Biosensors and Bioelectronics* 2010, 25, 1941-1946.

Lee, J.-S.; Lytton-Jean, A. K. R.; Hurst, S. J.; Mirkin, C. A. Silver nanoparticle—oligonucleotide conjugates based on DNA with triple cyclic disulfide moieties. *Nano Lett.* 2007, 7, 2112-2115.

Letsinger, R. L.; Elghanian, R.; Viswanadham, G.; Mirkin, C. A. Use of a steroid cyclic disulfide anchor in constructing gold nanoparticle—oligonucleotide conjugates. *Bioconjugate Chem.* 2000, 11, 289-291.

Li, F.; Zhang, J.; Cao, X.; Wang, L.; Li, D.; Song, S.; Ye, B.; Fan, C. Adenosine detection by using gold nanoparticles and designed aptamer sequences. *Analyst* 2009, 134, 1355-1360.

Li, H., Rothberg, L.J. Label-Free Colorimetric Detection of Specific Sequences in Genomic DNA Amplified by the Polymerase Chain Reaction. *J. Am. Chem. Soc.* 2004, 126, 10958-10961.

Li, J., Deng, T., Chu, X., Yang, R., Jiang, J., Shen, G., Yu, R. Rolling Circle Amplification Combined with Gold Nanoparticle Aggregates for Highly Sensitive Identification of Single-Nucleotide Polymorphisms. *Anal. Chem.* 2010, 82, 2811-2816.

Li, Z.; Jin, R.; Mirkin, C. A.; Letsinger, R. L. Multiple thiol-anchor capped DNA—gold nanoparticle conjugates. *Nucleic Acids Res.* 2002, 30, 1558-1562.

Liu, J.; Lu, Y. A colorimetric lead biosensor using DNAzyme-directed assembly of gold nanoparticles. *J. Am. Chem. Soc.* 2003, 125, 6642-6643.

Liu, J.; Lu, Y. Fast Colorimetric Sensing of Adenosine and Cocaine Based on a General Sensor Design Involving Aptamers and Nanoparticles. *Angew. Chem. Int. Ed.* 2006, 45, 90-94.

Liu, S.; Han, M. Synthesis, functionalization, and bioconjugation of monodisperse, silica-coated gold nanoparticles: Robust bioprobes. *Adv. Funct. Mater.* 2005, 15, 961-967.

Liu, S.; Zhang, Z.; Han, M. Gram-scale synthesis and biofunctionalization of silica-coated silver nanoparticles for fast colorimetric DNA detection. *Anal. Chem.* 2005, 77, 2595-2600.

Liz-Marzan, L. M.; Giersig, M.; Mulvaney, P. Synthesis of Nanosized Gold—Silica Core—Shell Particles. *Langmuir* 1996, 12, 4329-4335.

Medley, C. D.; Smith, J. E.; Tang, Z.; Wu, Y.; Bamrungsap, S.; Tan, W. Gold nanoparticle-based colorimetric assay for the direct detection of cancerous cells. *Anal. Chem.* 2008, 80, 1067-1072.

Mirkin, C. A.; Letsinger, R. L.; Mucic, R. C.; Storhoff, J. J. A DNA-based method for rationally assembling nanoparticles into macroscopic materials. *Nature* 1996, 382, 607-609.

Ou, L.-J.; Jin, P.-Y.; Chu, X.; Jiang, J.-H.; Yu, R.-Q. Sensitive and visual detection of sequence-specific DNA-binding protein via a gold nanoparticle-based colorimetric biosensor. *Anal. Chem.* 2010, 82, 6015-6024.

Rosi, N. L.; Giljohann, D. A.; Thaxton, C. S.; Lytton-Jean, A. K. R.; Han, M. S.; Mirkin, C. A. Oligonucleotide-modified gold nanoparticles for intracellular gene regulation. *Science* 2006, 312, 1027-1030.

Sato, K., Hosokawa, K., Maeda, M. Rapid Aggregation of Gold Nanoparticles Induced by Non-Cross-Linking DNA Hybridization. *J. Am. Chem. Soc.* 2003, 125, 8102-8103.

Sato, K., Hosokawa, K., Maeda, M. Non-cross-linking gold nanoparticle aggregation as a detection method for single-base substitutions. *Nucl. Acids Res.* 2005, 33(1), e4, doi:10.1093/nar/gni007.

Schroedter, A.; Weller, H.; Eritja, R.; Ford, W. E.; Wessels, J. M. Biofunctionalization of silica-coated CdTe and gold nanocrystals. *Nano Lett.* 2002, 2, 1363-1367.

Sharma, J.; Chhabra, R.; Liu, Y.; Ke, Y.; Yan, H. DNA-templated self-assembly of two-dimensional and periodical gold nanoparticle arrays. *Angew. Chem. Int. Ed.* 2006, 45, 730-735.

Sharma, J.; Chhabra, R.; Yan, H.; Liu, Y. A facile in situ generation of dithiocarbamate ligands for stable gold nanoparticle—oligonucleotide conjugates. *Chem. Commun.* 2008, 2140-2142.

Shorhoff, J.J., Elghanian, R., Mucic, R.C., Mirkin, C.A., Letsinger, R.L. One-Pot Colorimetric Differentiation of Polynucleotides with Single Base Imperfections Using Gold Nanoparticle Probes. *J. Am. Chem. Soc.* 1998, 120, 1959-1964.

Tan, E., Wong, J., Nguyen, D., Zhang, Y., Erwin, B., Van Ness, L.K., Baker, S.M., Galas, D.J., Niemz, A. Isothermal DNA Amplification Couples with DNA Nanosphere-Based Colorimetric Detection. *Anal. Chem.* 2005, 77, 7984-7992.

Thompson, D. G.; Enright, A.; Faulds, K.; Smith, W. E.; Graham, D. Ultrasensitive DNA detection using oligonucleotide—silver nanoparticle conjugates. *Anal. Chem.* 2008, 80, 2805-2810.

Wong, J.K.F., Yip, S.P., and Lee, T.M.H. Closed-Tube Colorimetric Polymerase Chain Reaction Using Silica-Modified Oligonucleotide-Gold Nanoparticle Probe. DOI: 10.1002/anie.200((will be filled in by the editrial staff)).

Wong, J.K.F., Yip, S.P., and Lee, T.M.H. Ultra-Stable Oligonucleotide-Gold and-Silver Nanoparticle Conjugates Prepared by a Facile Silica Reinforcement Method. *Nano Res.* 2012, 5(9):585-594, DOI 10.1007/s12274-012-0244-z, including Electronic Supplementary Material (4 pages).

Wong, J.K.F., Yip, S.P., and Lee, T.M.H. Silica-Modified Oligonucleotide-Gold Nanoparticle Conjugate Enables Closed-Tube

(56) References Cited

OTHER PUBLICATIONS

Colorimetric Polymerase Chain Reaction. *Small* 2012, 8, No. 2, 214-219 and Supporting Information for Small, DOI 10.1002/smll.201101925.

Xu, W., Xue, X., Li, T., Zeng, H., Liu, X. Ultrasensitive and Selective Colorimetric DNA Detection by Nicking Endonuclease Assisted Nanoparticle Amplification. *Angew. Chem. Int. Ed.* 2009, 48, 6849-6852.

Zhao, W.; Gao, Y.; Kandadai, S. A.; Brook, M. A.; Li, Y. DNA polymerization on gold nanoparticles through rolling circle amplification: Towards novel scaffolds for three-dimensional periodic nanoassemblies. *Angew. Chem. Int. Ed.* 2006, 45, 2409-2413.

Zhao, W.; Chiuman, W.; Brook, M. A.; Li, Y. Simple and rapid colorimetric biosensors based on DNA aptamer and noncrosslinking gold nanoparticle aggregation. *ChemBioChem* 2007, 8, 727-731.

Zhao, W.; Lam, J. C. F.; Chiuman, W.; Brook, M. A.; Li, Y. Enzymatic cleavage of nucleic acids on gold nanoparticles: A generic platform for facile colorimetric biosensors. *Small* 2008, 4, 810-816.

\* cited by examiner

5'-HS-(CH2)6-(OCH2CH2)6-GCAATAAACTCAACAGGAGCAG-3'

MPTMS: (3-mercaptopropyl)trimethoxysilane

SEQUENCE LISTING

<160> NUMBER OF SEQ ID NOS: 5

<210> SEQ ID NO 1
<211> LENGTH: 22
<212> TYPE: DNA
<213> ORGANISM: Artificial
<220> FEATURE:
<223> OTHER INFORMATION: Origin of artificial or unknown sequence:
      Primer
<220> FEATURE:
<221> NAME/KEY: misc_feature
<222> LOCATION: (1)..(1)
<223> OTHER INFORMATION: n is HS-(CH2)6-(OCH2CH2)6-guanine

<400> SEQUENCE: 1
ncaataaact caacaggagc ag                                            22

<210> SEQ ID NO 2
<211> LENGTH: 22
<212> TYPE: DNA
<213> ORGANISM: Artificial
<220> FEATURE:
<223> OTHER INFORMATION: Origin of artificial or unknown sequence:
      Primer
<220> FEATURE:
<221> NAME/KEY: misc_feature
<222> LOCATION: (1)..(1)
<223> OTHER INFORMATION: n is HS-(CH2)6-(OCH2CH2)6-guanine
<220> FEATURE:
<221> NAME/KEY: misc_feature
<222> LOCATION: (22)..(22)
<223> OTHER INFORMATION: n is guanosine diphosphate

<400> SEQUENCE: 2
ncaataaact caacaggagc an                                            22

<210> SEQ ID NO 3
<211> LENGTH: 22
<212> TYPE: DNA
<213> ORGANISM: Artificial
<220> FEATURE:
<223> OTHER INFORMATION: Origin of artificial or unknown sequence:
      Primer

<400> SEQUENCE: 3
ctgctcctgt tgagtttatt gc                                            22

```
<210> SEQ ID NO 4
<211> LENGTH: 21
<212> TYPE: DNA
<213> ORGANISM: Artificial
<220> FEATURE:
<223> OTHER INFORMATION: Origin of artificial or unknown sequence:
      Primer

<400> SEQUENCE: 4
gcgaacaatt cagcggcttt a                                              21

<210> SEQ ID NO 5
<211> LENGTH: 22
<212> TYPE: DNA
<213> ORGANISM: Artificial
<220> FEATURE:
<223> OTHER INFORMATION: Origin of artificial or unknown sequence:
      Primer
<220> FEATURE:
<221> NAME/KEY: misc_feature
<222> LOCATION: (1)..(1)
<223> OTHER INFORMATION: n is HS-(CH2)6-(OCH2CH2)6-guanine
<220> FEATURE:
<221> NAME/KEY: misc_feature
<222> LOCATION: (22)..(22)
<223> OTHER INFORMATION: n 6-FAM-label guanine nucleobase

<400> SEQUENCE: 5
ncaataaact caacaggagc an                                             22
```

ULTRA-STABLE OLIGONUCLEOTIDE-GOLD AND-SILVER NANOPARTICLE CONJUGATES AND METHOD OF THEIR PREPARATION

CROSS REFERENCE OF RELATED APPLICATION

This application claims benefit from U.S. Provisional Application No. 61/510,056 filed Jul. 20, 2011, the content of which is incorporated herewith by reference in its entirety.

FIELD OF THE INVENTION

The present invention relates to macromolecule-functionalized nanomaterials in the field of nanobiotechnology. Particularly, it relates to oligonucleotide-gold and -silver nanoparticle conjugates.

BACKGROUND OF THE INVENTION

Oligonucleotide—nanoparticle conjugates have attracted considerable interest because of an example of such conjugates explored by Mirkin and co-workers, who demonstrated a colorimetric DNA detection technique by using oligonucleotide-gold nanoparticle (AuNP) conjugates in the 1990s. The oligonucleotide offers target sequence-specific recognition capability and AuNP imparts solution color change in response to hybridization with the target. Dispersed oligonucleotide-AuNP conjugates appear red due to their characteristic surface plasmon resonance (SPR) absorption band (with absorption peak at ~520 nm). Upon target hybridization, cross-linking of two sets of conjugates results in particle aggregation and the reduction in interparticle distance causes a red shift of the SPR absorption band, hence the solution color turns purple. Alternatively, a non-cross-link method was designed by Maeda and co-workers that a single set of conjugates aggregated when hybridized with a perfectly complementary target under appropriate salt concentration (i.e., 0.5-2.5 M sodium chloride (NaCl)). Using specially designed sequences (e.g., DNAzyme and aptamer), oligonucleotide-AuNP conjugates have been utilized for the detection of numerous non-nucleic acid analytes, including metal ions, small molecules, proteins, and cells. As another example, oligonucleotide-silver nanoparticle (AgNP) conjugates were also be used for highly sensitive colorimetric detection as its extinction coefficient is larger than that of AuNP. Apart from diagnostics, these oligonucleotide-nanoparticle conjugates, in particular AuNPs, have proved to be very useful for therapeutics (e.g., gene and chemodrug delivery), as well as for the construction of DNA-templated nanostructures.

The most common method of preparing oligonucleotide-AuNP and -AgNP conjugates is by chemisorption of monothiol-modified oligonucleotide onto nanoparticle's surface. However, the chemisorbed oligonucleotide is known to be susceptible to displacement reaction by thiol-containing small molecules (e.g., dithiothreitol (DTT) and mercaptoethanol, frequently used ingredients in enzymatic reaction buffers) as well as to thermal desorption. This stability problem, if not solved, would seriously limit their applications. For example, when a significant portion of the oligonucleotide is desorbed from the AuNP surface, particle aggregation occurs and thus the solution color turns purple even in the absence of any targets. In 0.1 M DTT, this happens within a few minutes. To address this issue, Mirkin and co-workers prepared conjugates with steroid cyclic disulfide and trihexylthiol anchors, which exhibited greatly enhanced stability toward DTT (no aggregation for 2 and 8 hours, respectively). Nevertheless, these oligonucleotides were much more expensive because their syntheses required non-standard phosphoramidites with lower coupling yields. In view of this, Graham and co-workers reported the synthesis of thioctic acid-modified oligonucleotide via treatment of standard 3'-amino-modifier C7 controlled pore glass solid support with N-hydroxysuccinimidyl ester of thioctic acid while Liu and co-workers reported the synthesis of dithiocarbamate-modified oligonucleotide by means of reaction between amino-modified oligonucleotide and carbon disulfide. These two disulfide-linked conjugates had similar stability in DTT as the steroid cyclic disulfide-linked conjugates. Analogous to thiol-gold (S—Au) linkage, thiol-modified oligonucleotide can be conjugated to AgNP via thiol-silver (S—Ag) linkage, but with lower binding affinity. Triple cyclic disulfide and thioctic acid were successfully employed to enhance the stability of oligonucleotide-AgNP conjugates.

Regarding thermal desorption, the S—Au and S—Ag linkages are heat labile. For monothiol-linked oligonucleotide-AuNP conjugates, oligonucleotide desorption occurs readily at a temperature higher than 70° C. This prohibits their utilization in high temperature processes. One example is polymerase chain reaction (PCR), which is the most widely used method to amplify a specific DNA sequence and plays an important role in numerous applications including clinical diagnostics, environmental surveillance, food monitoring, forensic analysis, biowarfare agent detection, as well as biological research. It involves repeated cycling at three temperatures (i.e., 94° C. for template/amplicon denaturation, ~55° C. for primer annealing, and 72° C. for primer extension). The amount of the specific sequence is doubled at each thermal cycle, hence a single copy of the template ends up in million (20 cycles) to billion (30 cycles) copies of the amplicon. Highly sensitive colorimetric detection of PCR products with oligonucleotide-AuNP conjugates was reported. Nevertheless, post-amplification open-tube addition of the conjugates was unavoidable because they could not withstand the thermal cycling process, which posed a high risk of carryover contamination. Associated with the oligonucleotide desorption during PCR is the non-specific adsorption of Taq DNA polymerase onto the exposed AuNP surface and thus the amplification reaction is inhibited.

In view of the aforementioned stability issues and complicated and expensive solutions available in the art, there is a clear need for a new method of stabilizing oligonucleotide-AuNP and -AgNP conjugates that is easy-to-perform and inexpensive.

SUMMARY OF THE INVENTION

It is an objective of the present invention to provide an easy-to-use, effective, yet inexpensive method for stabilization of conjugates between oligonucleotide and AuNP or AgNP. As another objective of the present invention, there is provided highly stabilized oligonucleotide-AuNP and -AgNP conjugates, capable of being used under various severe conditions (such as harsh chemical and high temperature) necessary for particular applications.

According to one aspect of the present invention, there is provided a method of stabilizing conjugates between macromolecule and nanoparticle, comprising the steps of: (a) chemisorbing/adsorbing a plurality of macromolecules onto the surface of a nanoparticle; and (b) coating a thin reinforcement/entrapment layer (a single or few monolayers) on the particle surface after the macromolecules already being chemisorbed/adsorbed thereon. For oligonucleotide-AuNP and -AgNP conjugates, the reinforcement layer is preferably a silica layer formed by using (3-mercaptopropyl)trimethoxysilane ("MPTMS" hereinafter). If necessary, the macromolecules may be functionalized so that they are capable of being sufficiently chemisorbed/adsorbed onto the surface of the nanoparticles, for example, the thiol-modification of oligonucleotides. While in the present invention disclosed herewith, oligonucleotides as macromolecules and gold (Au) and silver (Ag) as materials of nanoparticles are presented as examples for illustrating the principles of the present invention, people of ordinary skill in the art may find other macromolecules and materials of nanoparticles in practicing the present invention. For example, other biopolymers (e.g., aptamer, small interfering RNA (siRNA), and peptide/protein) and synthetic polymers (e.g., polyethylene glycol (PEG)) along with other metal, metal oxide (e.g., iron oxide), and semiconducting (e.g., CdSe/ZnS core/shell) nanoparticles can be used. As long as the macromolecules used can be chemisorbed/adsorbed/linked/attached to the nanoparticles used and the attachment needs to be stabilized, the method of the present invention may be applicable. Exemplary linkages include thiol-Au, amino-Au, thiol-Ag, diol-iron oxide, amino-iron oxide, carboxyl-iron oxide, and thiol-CdSe/ZnS. It should be noted that the present invention is applicable to different shapes/forms of nanomaterials such as nanoparticle, core/shell, nanoshell, and nanorod. Central to the present invention is the reinforcement/entrapment layer that features high binding affinity with the nanoparticle's surface and forms a cross-linked network on the macromolecule-nanoparticle conjugate surface. Take the silica layer formed by using MPTMS as an example, the mercapto groups of MPTMS molecules chemisorb onto AuNP/AgNP vacant surface sites (i.e., places not occupied by macromolecules), followed by hydrolysis and polycondensation of the trimethoxysilyl groups, forming a single or a few silica monolayers. This thin cross-linked silica network entraps and reinforces the S—Au/Ag linkages of the chemisorbed oligonucleotides, thereby enhancing the conjugates' chemical and thermal stabilities. In fact, other reinforcement chemistries can be envisaged by people of ordinary skill in the art. Two generic types of reinforcement precursor molecules are given herein to illustrate the concepts. The first one is similar to the MPTMS precursor with the following structure:

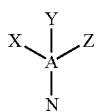

where A is a central atom such as silicon and carbon. It is understood that the valence of the central atom needs not be limited to 4. N is a chemical group that has high affinity with the nanomaterial of interest. Note that there can be more than one N group linked to the central atom. X, Y, and Z are groups (at least two) that can form cross-link to entrap the linkages of the macromolecule-nanoparticle conjugates. Different cross-link mechanisms can be employed such as chemical, photo, and thermal means. The second type of reinforcement molecules is oligomer with the following structure:

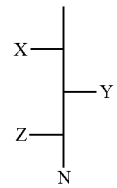

One example would be oligo(acryloxysuccinimide) where X, Y, and Z are succinimide groups, followed by chemical cross-linking with a molecule with at least two amine groups (e.g., hexamethylenediamine). The cross-link reaction can be achieved by a two-component approach (i.e., a molecule with high affinity with the nanomaterial is first immobilized, followed by the addition of another molecule that can cross-link with the first molecule to form a thin reinforcement layer) or by direct interactions between the oligomer molecules.

According to another aspect of the present invention, there is provided a macromolecule-nanoparticle conjugate which is highly stabilized under severe conditions. The conjugate of macromolecule-nanoparticle, comprising a nanoparticle, a reinforcement layer covering the outer surface of the nanoparticle, and a plurality of macromolecules attached directly to the surface of the nanoparticle because the reinforcement layer is formed after the macromolecules already being attached to the particle's surface so that a portion of the chain of the macromolecules is within the reinforcement layer which can then exert the effect of anchoring the macromolecules to the nanoparticle's surface. Preferably, the macromolecules are oligonucleotides which may be pre-functionalized for better attachment to the nanoparticle's surface. The nanoparticle is formed from gold or silver.

The stabilized conjugates may be used for in vitro diagnostic platforms, for example, closed-tube colorimetric PCR and other isothermal amplification reactions (especially those with thiol-containing stabilizers in the reaction buffers). They may also be used for in vivo imaging and drug delivery systems. There are currently numerous nano-contrast agents and drug-loaded nanocarriers that are based on macromolecule-nanoparticle conjugates. The macromolecules can offer recognition capability (e.g., oligonucleotide, aptamer, peptide, and antibody) and therapeutic function (e.g., siRNA), prolong blood circulation (e.g., PEG), and serve as carriers for contrast agents and/or drug molecules. The nanoparticles can have inherent imaging contrast properties (e.g., AuNP for X-ray imaging, iron oxide nanoparticle for magnetic resonance imaging, and CdSe/ZnS for fluorescence imaging) and therapeutic function (e.g., Au nanoshell and nanorod for photohyperthermia), and serve as carriers for contrast agents and/or drug molecules.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

Figure 1:
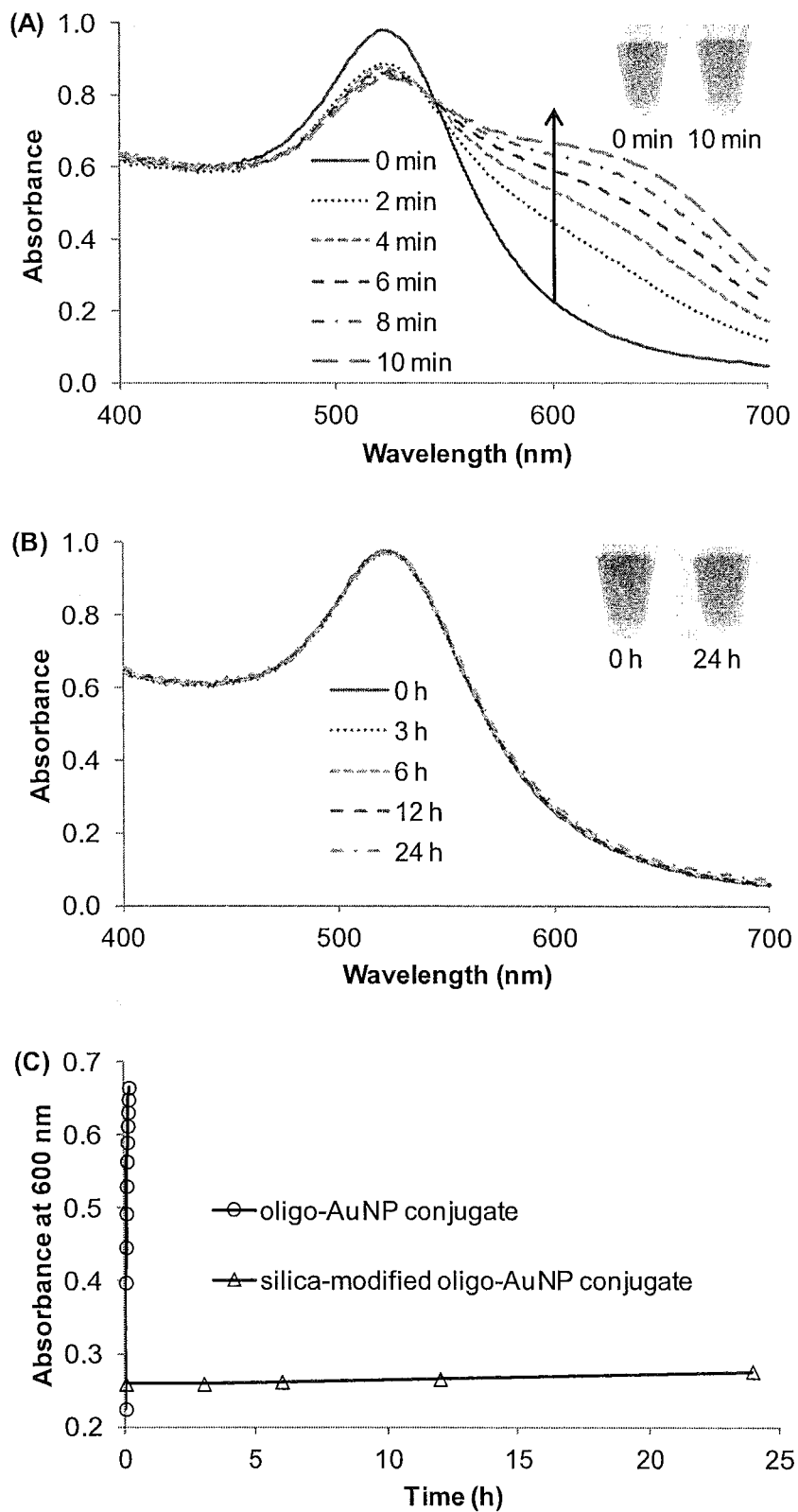
FIG. 1 presents the stability test results for the oligonucleotide-AuNP and silica-modified oligonucleotide-AuNP conjugates in 10 mM DTT. UV-vis spectra of (A) the oligonucleotide-AuNP conjugate and (B) the silica-modified oligonucleotide-AuNP conjugate. Insets are photographs showing the colors of the samples at different times. Arrow in (A) indicates the increase in absorbance at 600 nm with time. (C) Plots of absorbance at 600 nm versus time in (A) and (B).

In connection with drawings, the following description of some particular embodiments are provided to describe details of the invention and to illustrate the principles underlying the present invention, with which people of ordinary skill in the art would be enabled to come up other variations within the scope of the present inventions.

For this particular embodiment, the following materials and instrument were employed.

Hydrochloric acid (HCl), nitric acid ($HNO_3$), hydrogen tetrachloroaurate(III) solution ($HAuCl_4$), sodium citrate tribasic dihydrate, DTT, sodium phosphate dibasic heptahydrate ($Na_2HPO_4 \cdot 7H_2O$), sodium phosphate monobasic monohydrate, NaCl, 2-mercaptoethanol, MPTMS, potassium chloride (KCl), potassium phosphate monobasic ($KH_2PO_4$), NaCN, tris(hydroxymethyl)amino-methane (Tris), boric acid, ethylenediaminetetraacetic acid disodium salt dihydrate (EDTA), and ethidium bromide were purchased from Sigma-Aldrich (St. Louis, Mo., USA). Nitrocellulose membrane (0.8 µm) was purchased from Millipore (Billerica, Mass., USA). All oligonucleotides were purchased from Integrated DNA Technologies (Coralville, Iowa, USA) and were HPLC-purified. Desalting column (illustra MicroSpin G-25) was purchased from GE Healthcare (Piscataway, N.J., USA). AgNPs of diameter 30 nm (PELCO BioPure citrate-capped silver colloids) were purchased from Ted Pella (Redding, Calif., USA). All solutions used in PCR were prepared with UltraPure DNase/RNase-free distilled water from Invitrogen (Carlsbad, Calif., USA). All PCR and gel electrophoresis reagents were also purchased from Invitrogen, unless otherwise stated. All reagents were used as received. All solutions were prepared with ultrapure water (18.2 MΩ·cm) from a Milli-Q Advantage A10 System (Millipore).

UV-vis spectra were measured using an Ultrospec 2100 pro UV/visible spectrophotometer (GE Healthcare). Centrifugation was performed with an Eppendorf Microcentrifuge 5415 D (Eppendorf, Germany). Shaking was performed with a Thermomixer compact (Eppendorf). Real-time fluorescence measurements were carried out using an Applied Biosystems 7500 Real-Time PCR System (Applied Biosystems, Carlsbad, Calif., USA). Heating or PCR was carried out using a GeneAmp PCR System 9700 (Applied Biosystems). Gel image visualization/recording was performed using a ChemiGenius[2] gel imaging system (Syngene, Frederick, Md., USA).

Synthesis of 15 nm AuNPs

The synthesis of AuNPs was based on the protocol described by Natan and co-workers with minor modifications (Grabar, K. C., Freeman, R. G., Hommer, M. B. and Natan, M. J. (1995) Preparation and characterization of Au colloid monolayers. Anal. Chem., 67, 735-743). All glassware and magnetic stir bar used in the AuNP synthesis were cleaned with aqua regia (mixture of concentrated HCl and HNO$_3$ in a volume ratio of 3:1; because aqua regia is harmful and highly corrosive, and it must be handled with care in a fume hood), rinsed with water, and dried in an oven. A 30 mL solution of 0.01 wt % HAuCl$_4$ was boiled under reflux with vigorous stirring. Then, 3 mL of 1 wt % sodium citrate was added quickly. The solution color changed from pale yellow to deep red within minutes. Heating and stirring were continued for 10 min, followed by cooling to room temperature under stirring, and then the solution was filtered through a 0.8-μm nitrocellulose membrane. UV-vis spectrum of the as-prepared AuNPs was measured. According to the method reported by Haiss and co-workers, the size and concentration of AuNPs could be determined from the absorbance data (Haiss, W., Thanh, N. T. K., Aveyard, J. and Fernig, D. G. (2007) Determination of size and concentration of gold nanoparticles from UV-vis spectra. Anal. Chem., 79, 4215-4221). By calculating the ratio of the absorbance at the SPR peak ($A_{SPR,AuNP}$) to the absorbance at 450 nm ($A_{450,AuNP}$), the size of the AuNPs used in this work was determined to be ~15 nm. The concentration of the AuNP solution ($c_{AuNp}$, in M) was determined by the following equation:

$$c_{AuNP} = A_{450,AuNP}/\epsilon_{450,AuNP}$$

where $\epsilon_{450,AuNP}$ is the molar extinction coefficient of the 15 nm AuNPs at 450 nm (i.e., $2.18 \times 10^8$ M$^{-1}$cm$^{-1}$).

Preparation of Oligonucleotide-AuNP and -AgNP Conjugates

The preparation of oligonucleotide-AuNP conjugate was based on the protocol described by Mirkin and co-workers with minor modifications (Storhoff, J. J., Elghanian, R., Mucic, R. C., Mirkin, C. A. and Letsinger, R. L. (1998) One-pot colorimetric differentiation of polynucleotides with single base imperfections using gold nanoparticle probes. J. Am. Chem. Soc., 120, 1959-1964). The method was known in the art. Specifically, a thiol-modified oligonucleotide, 5'-HS—(CH$_2$)$_6$—(OCH$_2$CH$_2$)$_6$-GCAATAAACTCAACA-GGAGCAG-3' (SEQ ID NO.: 1), was treated with 0.1 M DTT in 0.2 M sodium phosphate buffer (pH 8.2) for 30 min. This activated oligonucleotide solution (i.e., with disulfur linkage cleaved) was purified by passing through a desalting column according to the manufacturer's instructions. Immediately afterward, the purified oligonucleotide was mixed with the AuNPs at a final concentration of 1.75 μM and 3.5 nM, respectively. They were incubated for 16 h, and then aged with 0.3 M NaCl/10mM sodium phosphate (pH 7.4) for 24 h. Next, the solution was centrifuged at 13,200 rpm for 30 min to remove excess oligonucleotide. The supernatant was discarded and the red oily precipitate (i.e., the oligonucleotide-AuNP conjugate) was redispersed in 10 mM sodium phosphate buffer (pH 7.4). The solution was centrifuged again and redispersed in water. UV-vis spectrum of the as-prepared oligonucleotide-AuNP conjugate was measured and the particle concentration was determined by the following equation:

$$c_{AuNP-conjugate} = c_{AuNP} \times (A_{SPR,AuNP\text{-conjugate}}/A_{SPR,AuNP})$$

To determine the immobilized oligonucleotide density, a 3'-6-FAM-labeled sequence was used (5'-HS—(CH$_2$)$_6$—(OCH$_2$CH$_2$)$_6$-GCAATAAACTCAACAGGAGCAG-6-FAM-3') (SEQ ID NO.: 5). The oligonucleotide-AuNP conjugate (2.5 nM) was treated with 2-mercaptoethanol (12 mM) in NaCl (0.3 M) and sodium phosphate (10 mM, pH 7.4) for 24 h under shaking at 1,400 rpm to release the chemisorbed oligonucleotide from the AuNP surface, followed by centrifugation (13,200 rpm for 30 min) and fluorescence measurement of the collected supernatant. The amount of the chemisorbed oligonucleotide was determined with reference to a standard curve and the immobilized oligonucleotide density (i.e., number of oligonucleotide strands per AuNP, n total,AuNP-conjugate) was calculated accordingly.

The preparation of oligonucleotide-AgNP conjugate was based on the protocol described by Graham and co-workers with minor modifications (Thompson, D. G., Enright, A., Faulds, K., Smith, E. and Graham, D. (2008) Ultrasensitive DNA detection using oligonucleotide-silver nanoparticle conjugates. Anal. Chem., 80, 2805-2810). The activated and purified oligonucleotide was mixed with AgNPs at a final concentration of 12.5 μM and 6.25 nM, respectively. They were incubated for 16 h, and then progressively brought to 2, 4, 8, 16, 32, 64, 100, 150 and 300 mM of NaCl by adding 0.33 M NaCl/11.11 mM sodium phosphate (pH 7.4) at 1 h interval. The final mixture was incubated for 24 h. Next, the solution was centrifuged and redispersed as above. Note that the color of the oligonucleotide-AgNP conjugate was yellow. UV-vis spectrum of the as-prepared oligonucleotide-AgNP conjugate was measured and the particle concentration was determined by the following equation:

$$c_{AgNP-conjugate} = c_{AgNP} \times (A_{SPR,AgNP\text{-conjugate}}/A_{SPR,AgNP})$$

where $c_{AgNP}$ and the corresponding $A_{SPR,AgNP}$ were available from the manufacturer.

Preparation of Silica-Modified Oligonucleotide-AuNP and -AgNP Conjugates

The oligonucleotide-AuNP conjugate was mixed with MPTMS at a final concentration of 1 nM and 0.1 mM, respectively, while the oligonucleotide-AgNP conjugate was mixed with MPTMS at a final concentration of 0.25 nM and 0.1 mM, respectively. The mixtures were shaken at 1,400 rpm for 24 h, and then supplied with 10 mM sodium phosphate (pH 7.4). After that, they were centrifuged and redispersed again as above. UV-vis spectra of the as-prepared silica-modified oligonucleotide-AuNP and -AgNP conjugates were measured and their particle concentrations were determined by the following equations:

$$c_{silica-AuNP-conjugate} = c_{AuNP} \times (A_{SPR,silica-AuNP\text{-conjugate}}/A_{SPR,AuNP})$$

$$c_{silica-AgNP-conjugate} = c_{AgNP} \times (A_{SPR,silica-AgNP\text{-conjugate}}/A_{SPR,AgNP})$$

To determine the oligonucleotide density of the silica-modified oligonucleotide-AuNP conjugate, the fluorescently labeled oligonucleotide-AuNP conjugate was used. The supernatant of the MPTMS-treated conjugate was collected and fluorescence measurement was performed to determine the amount of oligonucleotide displaced after the silica coating step. By subtracting the displaced amount from the immobilized amount, the oligonucleotide density of the silica-modified oligonucleotide-AuNP conjugate ($n_{total,silica-AuNP-conjugate}$) was obtained.

Chemical Stability Tests

Chemical stability tests of the oligonucleotide-AuNP and silica-modified oligonucleotide-AuNP conjugates (2.5 nM) as well as the oligonucleotide-AgNP and silica-modified oligonucleotide-AgNP conjugates (0.1 nM) were performed in phosphate-buffered saline (PBS: 137 mM NaCl, 2.7 mM KCl, 4.3 mM Na$_2$HPO$_4$.7H$_2$O, and 1.4 mM KH$_2$PO$_4$, pH 7.4) with 10 mM DTT or 2 mM NaCN. UV-vis spectra and solution colors were recorded at different time intervals.

Fluorescence characterization of the oligonucleotide desorption in DTT was performed using 3'-FAM-labeled oligonucleotide-AuNP and silica-modified 3'-FAM-labeled oligonucleotide-AuNP conjugates. The supernatants were collected for fluorescence measurement to determine the amounts of desorbed oligonucleotide at the end of the 3-h treatment ($n_{desorbed,2h}$). The amounts of oligonucleotide desorbed from the conjugates at different incubation times (in terms of the total immobilized amount, $n_{total}$, i.e., $n_{total,AuNP-conjugate}$ for the oligonucleotide-AuNP conjugate and $n_{total,silica-AuNP-conjugate}$ for the silica-modified oligonucleotide-AuNP conjugate) were determined by the following equation:

$$\%_{desorbed,t}=(F_t/F_{3h})\times(n_{desorbed,2h}/n_{total})\times100\%$$

where $\%_{desorbed,t}$ is the percentage of desorbed oligonucleotide at time t, and $F_t$ and $F_{3h}$ are the fluorescence readings at time t and 3-h, respectively. Note that the values of $n_{total,AuNP-conjugate}$ and $n_{total,silica-AuNP-conjugate}$ are different.

Hybridization Tests

The silica-modified oligonucleotide-AuNP conjugate (3.125 nM) was incubated in PBS with 10 mM DTT for 3 h. Then, 0.5 M NaCl and 0.2 μM complementary target (5'-CTGCTCCTGTTGAGTTTATTGC-3') (SEQ ID NO.: 3) were added, with a final conjugate concentration of 2.5 nM. Hybridization was allowed to proceed for 10 min. Finally, the solutions were heated at 94° C. for 1 min. UV-vis spectra and colorimetric results were recorded before and after hybridization, as well as after heat denaturation. For the silica-modified oligonucleotide-AgNP conjugate (0.1 nM), the complementary target (0.5 μM) was added together with DTT (10 μM), PBS, and 0.5 M NaCl. Hybridization and denaturation were carried out as above.

Thermal stability Tests

Thermal stability tests were performed using 3'-FAM-labeled oligonucleotide-AuNP and silica-modified 3'-FAM-labeled oligonucleotide-AuNP conjugates at different temperature settings. For constant temperature (i.e., 94, 72, or 55° C.), the sample contained the unmodified or silica-modified conjugate (2.5 nM), 1× PCR buffer (50 mM KCl, 20 mM Tris-HCl, pH 8.4), and MgCl$_2$ (6 mM). Fluorescence signal was acquired every 10 mM for 2 h. After that, the sample was centrifuged (13,200 rpm for 30 mM) and the supernatant was collected for fluorescence measurement to determine the amount of desorbed oligonucleotide at the end of the 2-h thermal treatment ($n_{desorbed,2h}$). The amount of oligonucleotide desorbed from the conjugate at different incubation times (in terms of the total immobilized amount, $n_{total}$) was determined by the following equation:

$$\%_{desorbed,t}=(F_t/F_{2h})\times(n_{desorbed,2h}/n_{total})\times100\%$$

where $\%_{desorbed,t}$ is the percentage of desorbed oligonucleotide at time t, and $F_t$ and $F_{2h}$ are the fluorescence readings at time t and 2-h, respectively. For PCR thermal cycling, the sample contained the unmodified or silica-modified conjugate (2.5 nM), 1× PCR buffer, MgCl$_2$ (6 mM), and dithiothreitol (5 μM). The thermal cycling profile used was identical to that described in the next PCR section. Fluorescence signal was collected at the extension step of each cycle. After thermal cycling, the sample was centrifuged (13,200 rpm for 30 mM) and the supernatant was collected for fluorescence measurement to determine the amount of desorbed oligonucleotide at the end of PCR ($n_{desorbed,end\ PCR}$). The amount of oligonucleotide desorbed from the conjugate at different cycle numbers (in terms of the total immobilized amount, $n_{total}$) was determined by the following equation:

$$\%_{desorbed,cycle}=(F_{cycle}/F_{end\ PCR})\times(n_{desorbed,end\ PCR}/n_{total})\times100\%$$

where $\%_{desorbed,cycle}$ is the percentage of desorbed oligonucleotide at a particular cycle, and $F_{cycle}$ and $F_{end\ PCR}$ are the fluorescence readings at the particular cycle and the end of PCR, respectively.

PCR

PCR mix comprised 1×PCR buffer, MgCl 2 (6 mM), dNTPs (0.2 mM each), Primer 1 (same as the complementary target: 5'-CTGCTCCTGTTGAGTTTATTGC-3' (SEQ ID NO.: 3), 0.2 μM), Primer 2 (5'-GCGAACAATTCAGCG-GCTTTA-3' (SEQ ID NO.: 4), 0.2 μM), Taq DNApolymerase (0.025 units/μL), template (ΦX174, $10^7$ copies) or no-template control, and nanoparticles (bare AuNPs, silica-modified AuNPs, oligonucleotide-AuNPconjugate, or silica-modified oligonucleotide-AuNP conjugate, 2.5 nM). Thermal cycling profile used was 94° C. for 1 min (initial denaturation); 25 cycles of 94° C. for 5 s (denaturation), 55° C. for 5 s (annealing), and 72° C. for 30 s (extension); and 72° C. for 2 min (final extension). The samples were cooled to room temperature before being taken out from the thermal cycler. Colorimetric results and UV-vis spectrawere recorded 40 min after PCR.

PCR products were analyzed by gel electrophoresis technique. The products (8 μL) were mixed with BlueJuice gel loading buffer (2 μL) and then loaded into wells of an agarose gel (3%) in 0.5×TBE buffer (45 mM Tris, 45 mM boric acid, 1 mM EDTA, pH 8.0). The gel was electrophoresed at 120 V for 1.5 h, followed by staining with ethidium bromide (0.5 μg/mL) for 10 min and results visualization.

Testing Results

It is known in the art that DTT readily displaces monothiol-modified oligonucleotide chemisorbed onto AuNP surface, resulting in irreversible particle aggregation. As shown in FIG. 1A, this caused a red shift and broadening of the SPR absorption band, with a slight decrease in absorbance at 520 nm and a large increase at longer wavelengths (600-650 nm). The color of the solution changed from red to grayish purple within a few minutes (insets of FIG. 1A). In a sharp contrast, if the monothiol-modified oligonucleotide-AuNP conjugate was treated with MPTMS, the UV-vis spectrum and solution color of the silica-modified oligonucleotide-AuNP conjugate remained unchanged even after 24-h incubation in 10 mM DTT (FIG. 1B). While not intending to be bound by any theory of action, it is believed that the MPTMS treatment may form a thin silica coating on the surface of the oligonucleotide-AuNP conjugate and such coating anchors the oligonucleotide onto the surface with much greater strength. Plots of the absorbance at 600 nm versus incubation time clearly revealed the enormous stability enhancement in DTT of the silica-modified oligonucleotide-AuNP conjugate (FIG. 1C). From the results it can be clearly seen that the silica-reinforced conjugate of the present invention compares favorably to conjugates prepared with bidentate and tridentate linkages, which are stabile in 10 mM DTT for 1-3 h and 8 h, respectively.

Figure 2:
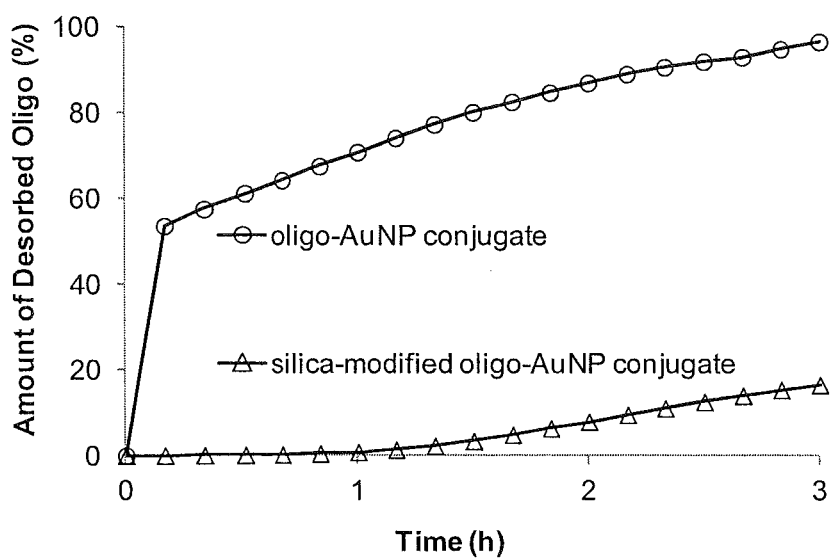
FIG. 2 presents the plots of the amounts of oligonucleotide desorbed from the oligonucleotide-AuNP and silica-modified oligonucleotide-AuNP conjugates as a function of incubation time in 10 mM DTT.

To quantitatively characterize the displacement reaction, the oligonucleotide was labeled with a fluorescent dye (6-FAM) and real-time fluorescence measurement during the DTT incubation period was performed. It is known in the art that fluorescence signal is low if the oligonucleotide is in the bound state as the emission of 6-FAM is efficiently quenched by the AuNP, and the signal increases upon the desorption of the oligonucleotide from the AuNP surface. It was found that 54% of the oligonucleotide was desorbed from the unmodified oligonucleotide-AuNP conjugate after 10-mM incubation in 10 mM DTT and nearly 0% from the silica-modified oligonucleotide-AuNP conjugate (FIG. 2). After 3-h incubation, the amounts increased to 97% and 17%, respectively. The results clearly indicate that, with the MPTMS treatment, the S—Au linkage becomes much more resistant to ligand exchange reaction by DTT.

Figure 3:
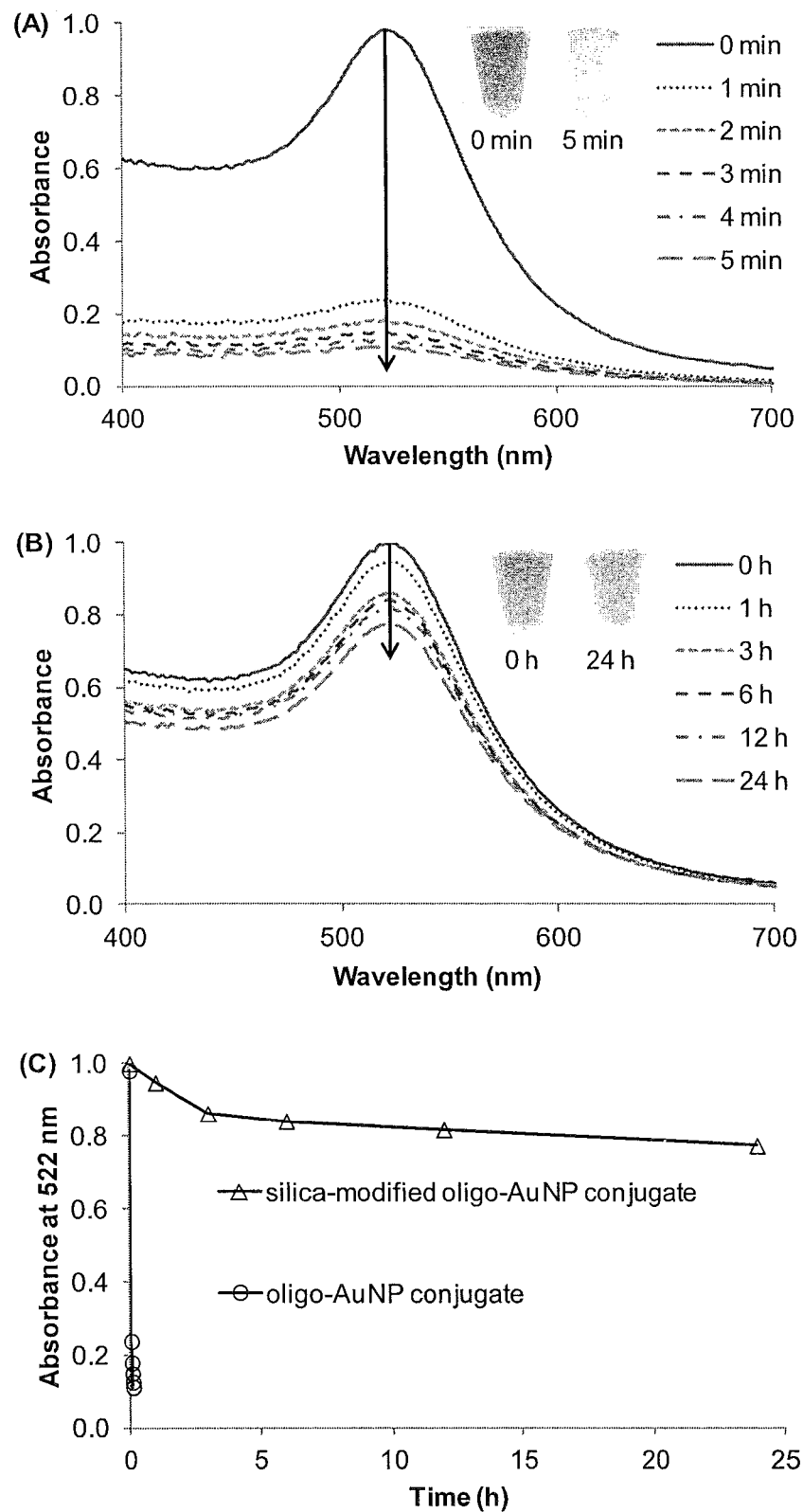
FIG. 3 presents the stability tests for the oligonucleotide-AuNP and silica-modified oligonucleotide-AuNP conjugates in 2 mM sodium cyanide (NaCN). UV-vis spectra of (A) the oligonucleotide-AuNP conjugate and (B) the silica-modified oligonucleotide-AuNP conjugate. Insets are photographs showing the colors of the samples at different times. Arrows indicate the decrease in absorbance at 522 nm with time. (C) Plots of absorbance at 522 nm versus time in (A) and (B).

To further support the existence of a silica layer, oxidative dissolution of AuNP core with NaCN was carried out. With 2 mM NaCN, the oligonucleotide-AuNP conjugate solution turned colorless in less than 1 mM (the SPR absorption peak diminished greatly, FIG. 3A), whereas the silica-modified oligonucleotide-AuNP conjugate solution remained red after 24-h incubation (the SPR absorption peak dropped by 23%, FIG. 3B). Plots of the absorbance at 522 nm versus incubation time manifest the significant improvement in chemical stability against oxidative dissolution of the AuNPs for the silica-modified oligonucleotide-AuNP conjugate (FIG. 3C). These data provide evidence that the silica coating serves as an effective diffusion barrier for the cyanide reactant and/or [Au(CN)$_2$]$^-$ product. In fact, it is likely that this coating also hinders DTT from approaching the AuNP surface and thus interacting with/displacing the S—Au linkage of the chemisorbed oligonucleotide.

Figure 4:
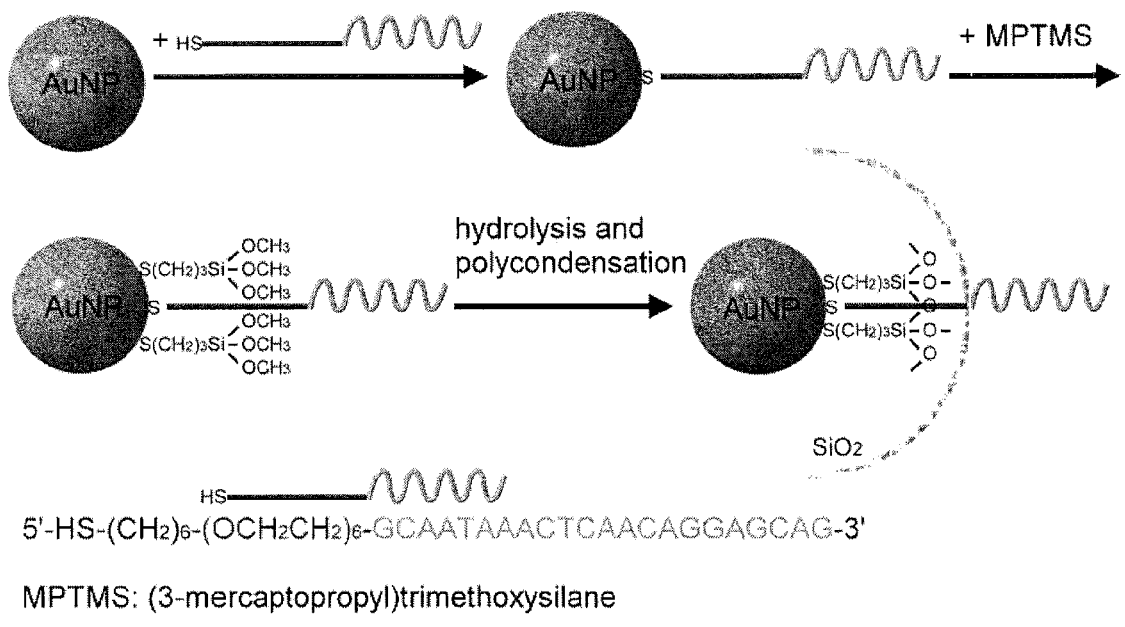
FIG. 4 presents a schematic illustration of the preparation procedures for the silica-modified oligonucleotide-AuNP conjugate as a particular embodiment of the present invention. SEQ ID NO: 1 is depicted.
Figure 5:
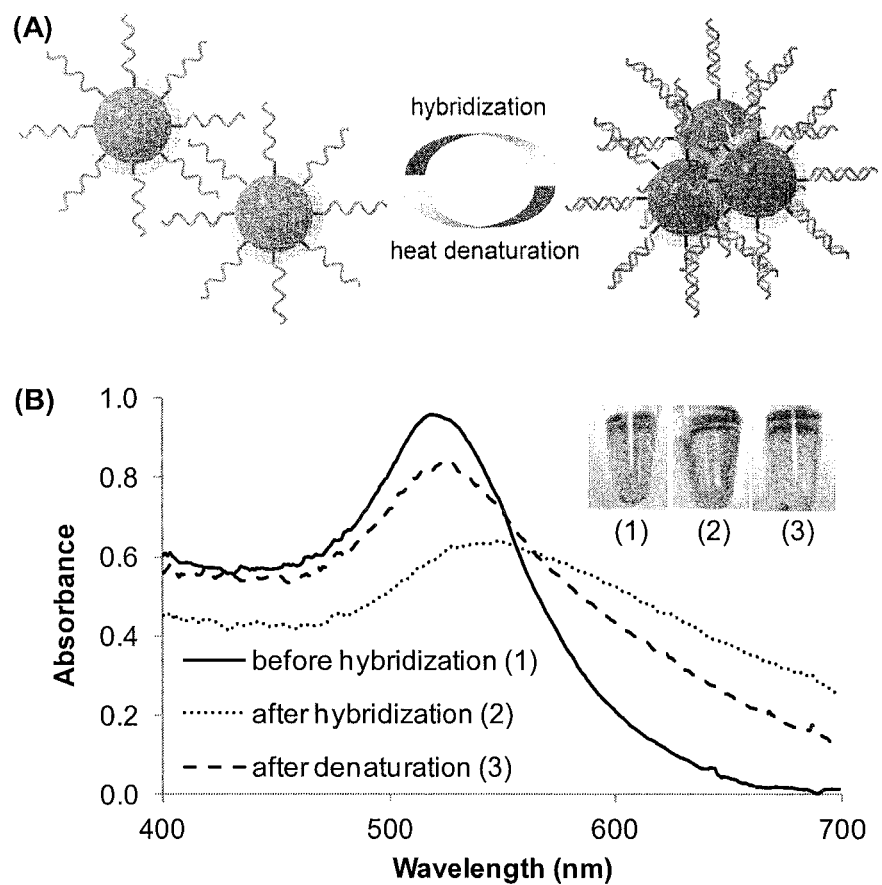
FIG. 5 presents (A) a schematic illustration of the hybridization-induced aggregation tests for the silica-modified oligonucleotide-AuNP conjugates; and (B) UV-vis spectra of the silica-modified oligonucleotide-AuNP conjugate (1) after incubation in DTT for 3 h (before hybridization); (2) after hybridization with the complementary target for 10 min; and (3) after denaturation/dehybridization at 94° C. for 1 min. Insets are photographs of the samples (1), (2), and (3).

In a previous study, a thick silica shell (75 nm) was first grown on AuNP, followed by surface functionalization with aldehyde groups and then covalent attachment of amino-modified oligonucleotides. Despite the potentially higher chemical stability, there was no color change in response to target hybridization due to the thick silica shell. In the present invention, thiol-modified oligonucleotide is first chemisorbed onto AuNP surface, followed by a thin silica coating (a single or few monolayers) with MPTMS (FIG. 4). This thin silica coating method was originally developed by Mulvaney and co-workers to render AuNP surface (without oligonucleotide) vitreophilic for subsequent controlled growth of thicker silica shell. The hybridization-induced color change property of the silica-modified oligonucleotide-AuNP conjugate of the present invention was tested using Maeda's non-cross-link approach. Before hybridization, the silica-modified oligonucleotide-AuNP conjugate was incubated in PBS with 10 mM DTT for 3 h. Consistent with the result in FIG. 1B, it remained stable with SPR absorption peak at 522 nm. Upon the addition of the complementary target and 0.5 M NaCl, the SPR absorption peak shifted to 549 nm and the solution color changed from red to purple within 10 min (FIG. 5). This can be explained by the lower stability of double-stranded conjugate against salt-induced aggregation than single-stranded counterpart. To further confirm such hybridization-induced color change, the double-stranded conjugate solution was heated at 94° C. for 1 min to effect dehybridization. As expected, the SPR absorption peak shifted back (525 nm) and the solution color returned to red.

Figure 6:
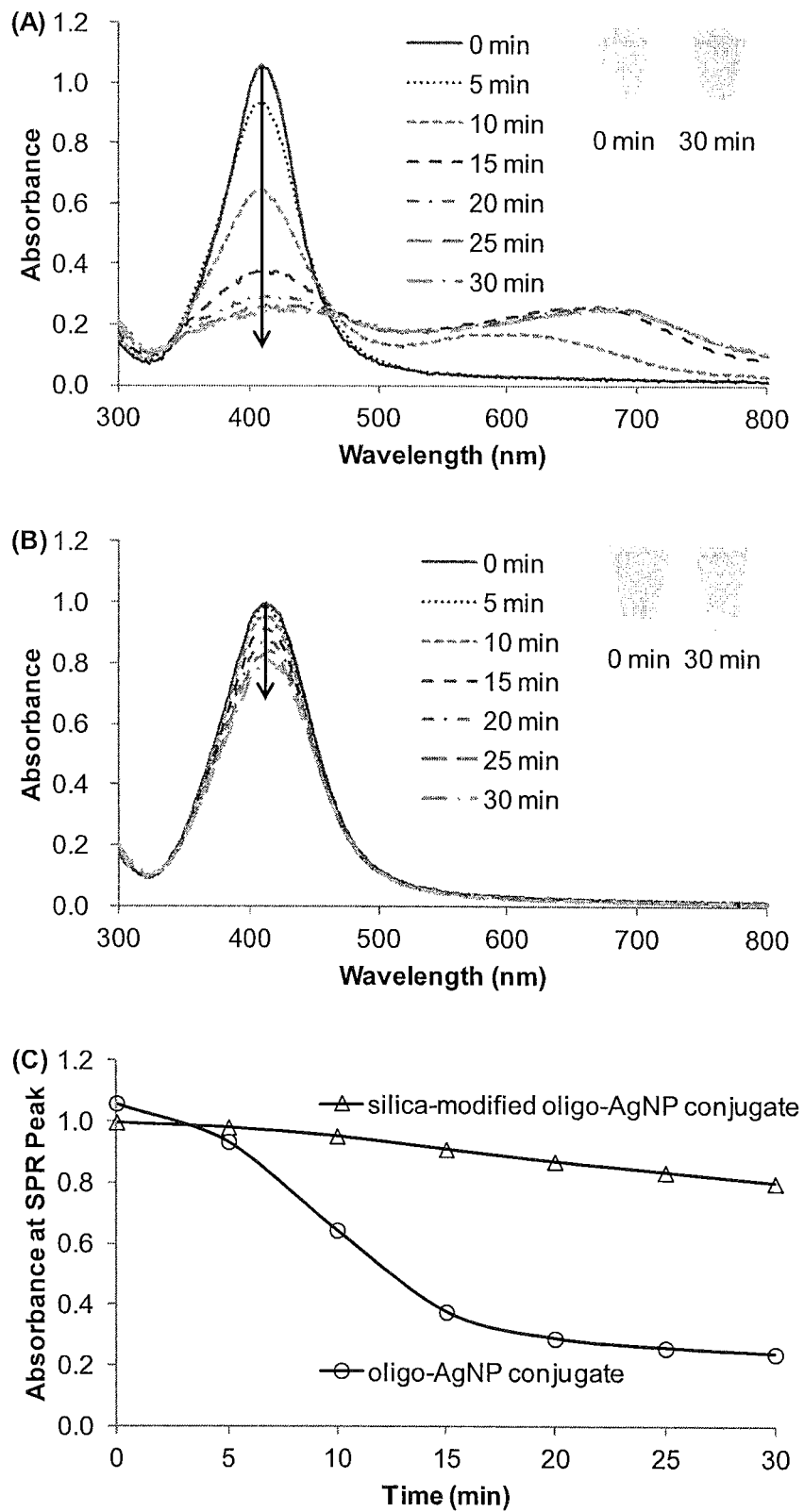
FIG. 6 presents the stability test results for the oligonucleotide-AgNP and silica-modified oligonucleotide-AgNP conjugates in 10 mM DTT. UV-vis spectra of (A) the oligonucleotide-AgNP conjugate and (B) the silica-modified oligonucleotide-AgNP conjugate. Insets are photographs showing the colors of the samples at different times. Arrows indicate the decrease in absorbance at SPR peaks (i.e., 410 nm and 414 nm for the oligonucleotide-AgNP and silica-modified oligonucleotide-AgNP conjugates, respectively) with time. (C) Plots of absorbance at SPR peaks versus time in (A) and (B).
Figure 7:
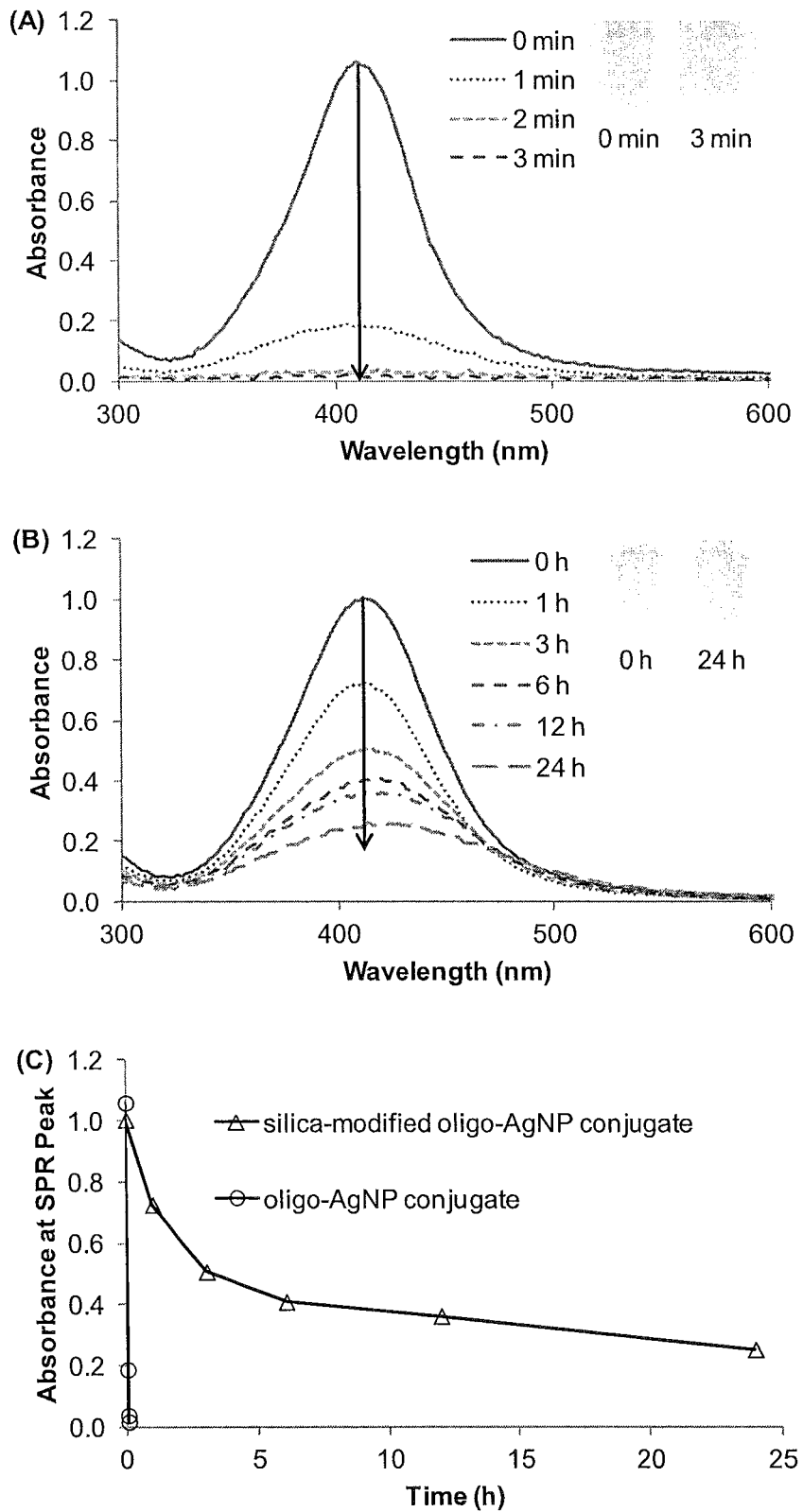
FIG. 7 presents the stability test results for the oligonucleotide-AgNP and silica-modified oligonucleotide-AgNP conjugates in 2 mM NaCN. UV-vis spectra of (A) the oligonucleotide-AgNP conjugate and (B) the silica-modified oligonucleotide-AgNP conjugate. Insets are photographs showing the colors of the samples at different times. Arrows indicate the decrease in absorbance at SPR peaks with time. (C) Plots of absorbance at SPR peaks versus time in (A) and (B).
Figure 8:
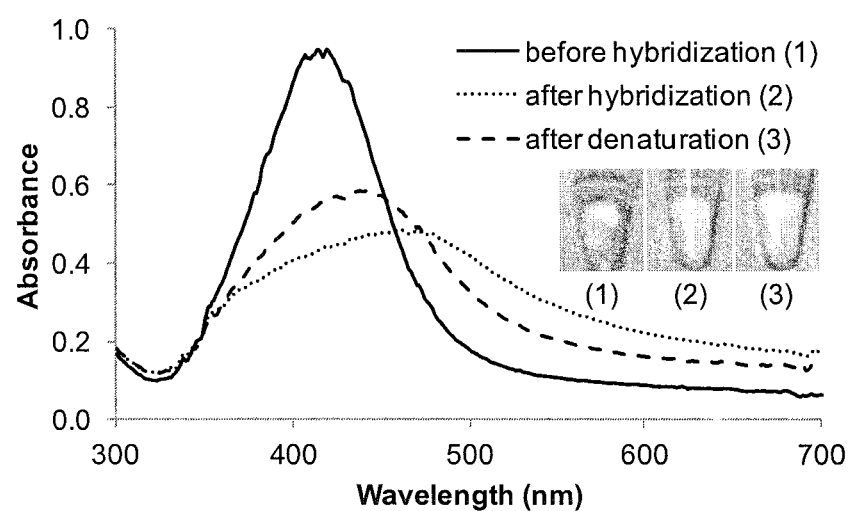
FIG. 8 presents UV-vis spectra of the silica-modified oligonucleotide-AgNP conjugate (1) before hybridization; (2) after hybridization with the complementary target in the presence of 10 µM DTT for 10 min; and (3) after denaturation/dehybridization at 94° C. for 1 min. Insets are photographs of the samples (1), (2), and (3).

Apart from the oligonucleotide-AuNP conjugate, the newly developed silica reinforcement method can be applied to other types of conjugates with linkage similar to S—Au. Oligonucleotide-AgNP conjugate has been successfully prepared using S—Ag linkage, but with limited stability in high salt concentration (up to 0.3 M NaCl as compared with higher than 2.5 M for oligonucleotide-AuNP conjugate) due to its low binding affinity. Also, it is not stable against DTT displacement. The stability, however, can be improved greatly by the present invention. As shown in FIG. 6A, dispersed oligonucleotide-Ag NP conjugate exhibited a characteristic SPR absorption peak at 410 nm and appeared yellow. When 10 mM DTT was added, particle aggregation took place within minutes. The absorbance at 410 nm decreased dramatically while that at longer wavelengths (>500 nm) increased and a new absorption peak at ~700 nm appeared. For silica-modified oligonucleotide-AgNP conjugate, the displacement reaction was much slower (the SPR absorption peak intensity decreased by 20% after 30-min incubation versus 77% for the unmodified conjugate) (FIG. 6B). Plots of the SPR absorption peak intensity versus incubation time illustrate the significant improvement offered by the silica coating against DTT-induced particle aggregation (FIG. 6C). In fact, the stability of the silica-modified oligonucleotide-AgNP conjugate is better than that of the conjugate prepared with bidentate linkage reported in the art. Nonetheless, the stability of the silica-modified oligonucleotide-AgNP conjugate is considerably lower than the silica-modified oligonucleotide-AuNP conjugate. This is understandable in that the low binding affinity of the S—Ag linkage would possibly result in a less compact silica layer. Stability test for AgNP dissolution by NaCN and hybridization test were also carried out for the silica-modified oligonucleotide-AgNP conjugate (FIG. 7 and FIG. 8, respectively). The results were consistent with those of the silica-modified oligonucleotide-AuNP conjugate for the stabilization effect.

Because the stabilization effect exemplified above is most likely due to the formation of a thin silica layer on the surfaces of nanoparticles, which can physically anchor the oligonucleotide onto the surface and may also serve as a barrier to fend off agents which can destabilize the attachment, this method can be readily extended, with no or minor modifications, to other conjugates between macromolecules and nanoparticles when stabilization needs to be improved in simple and inexpensive manner. For example, it can be extended to conjugates used in vitro diagnostics, especially enzymatic reactions that require DTT or mercaptoethanol as stabilizer and conjugates used in vivo imaging and therapeutic applications.

Figure 9:
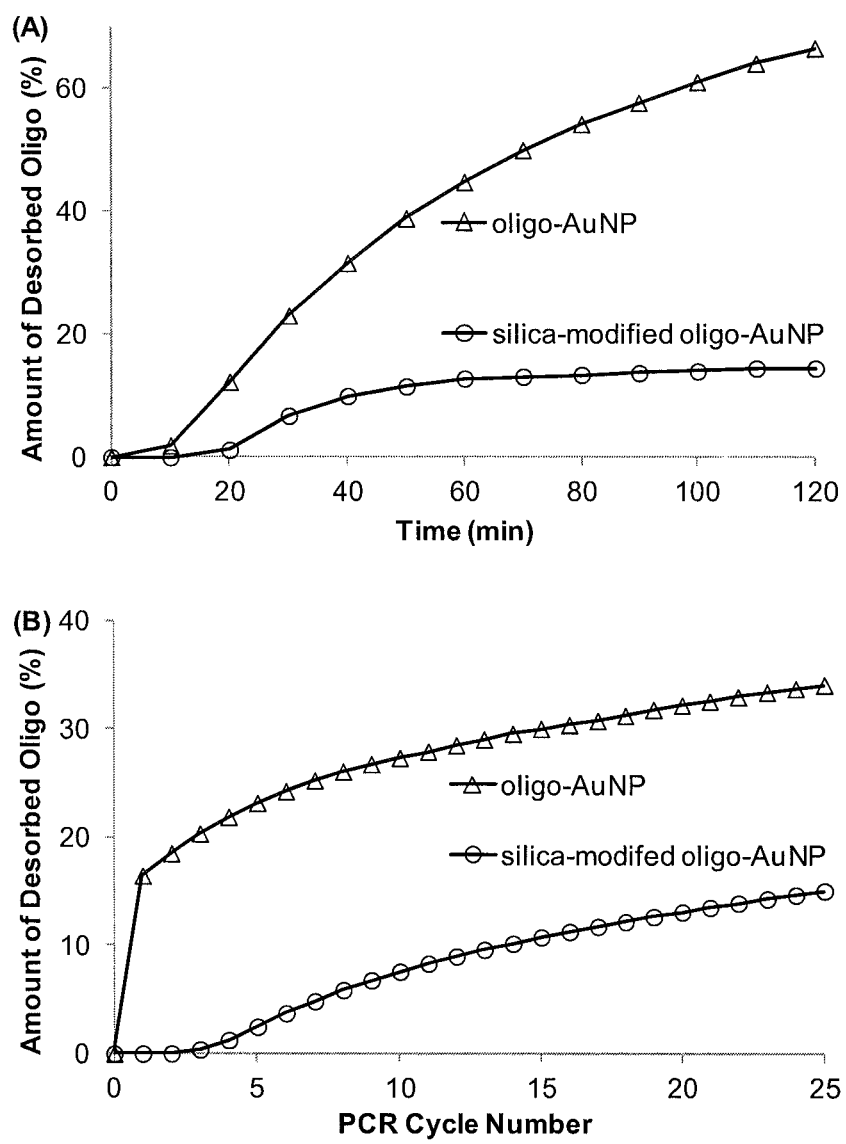
FIG. 9 presents the plots of the amounts of oligonucleotide desorbed from the oligonucleotide-AuNP and silica-modified oligonucleotide-AuNP conjugates (A) versus incubation time at 94° C. in 1× PCR buffer and (B) versus PCR cycle number in 1× PCR buffer with 5 µM DTT.

Regarding thermal stability, after 2-h incubation at 94° C. in 1× PCR buffer, 66% and 15% of the oligonucleotide was desorbed from the AuNP surface for the unmodified and silica-modified oligonucleotide-AuNP conjugates, respectively (FIG. 9A). When subjected to PCR thermal cycling in 1× PCR buffer with 5 µM DTT, the amounts of desorbed oligonucleotide for the unmodified and silica-modified oligonucleotide-AuNP conjugates were 34% and 15%, respectively.

Figure 10:
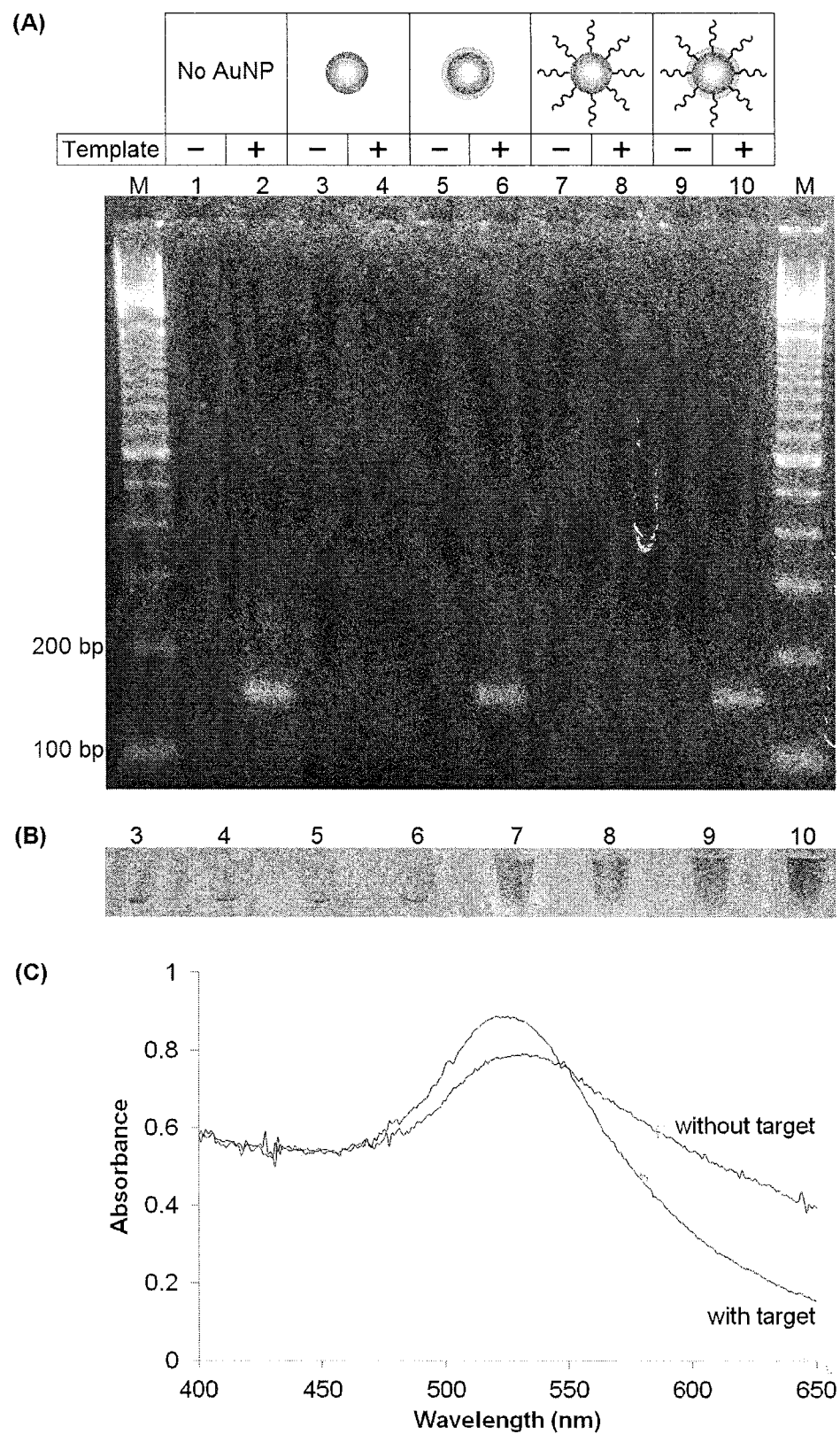
FIG. 10 presents (A) the gel electrophoresis results of the effects of different AuNPs on PCR amplification. The template used was φX174 ($10^7$ copies in each reaction) and the PCR product was 151 base pairs (bp) long. Lane M: marker; odd lanes were negative samples without the template while even lanes were positive samples with the template; lanes 1 and 2: controls without AuNPs; lanes 3 and 4: bare AuNPs; lanes 5 and 6: silica-modified AuNPs; lanes 7 and 8: oligonucleotide-AuNP conjugate; lanes 9 and 10: silica-modified oligonucleotide-AuNP conjugate. The MgCl2 and AuNP concentrations in the mixture were 6 mM (except the controls, 1.5 mM) and 2.5 nM, respectively. (B) Photograph of the samples 3-10 in (A) taken 40 min after PCR. (C) UV-vis spectra of the samples 9 and 10 in (B).

Another important issue is the inhibition of enzymatic reaction caused by the non-specific adsorption of enzyme onto AuNP surface. For example, the inclusion of 2.5 nM bare AuNPs in a PCR mixture inhibited the amplification reaction (FIG. 10A, lane 4, no PCR product band). Interestingly, when AuNPs were treated with MPTMS, a PCR product band was observed (lane 6), the intensity of which was comparable to that of the control (lane 2, without AuNPs). It is therefore apparent that the silica surface has negligible interaction with Taq DNA polymerase. Analogous to the bare AuNPs, PCR was inhibited for the oligonucleotide-AuNP conjugate (lane 8). This can be explained by the thermal desorption of the oligonucleotide and subsequent adsorption of Taq DNA polymerase onto the exposed AuNP surface. For the silica-modified oligonucleotide-AuNP conjugate, the PCR product band intensity was similar to that without AuNPs (lane 10 versus lane 2). This is attributed to the enhanced thermal stability and PCR compatibility offered by the silica coating.

Figure 11:
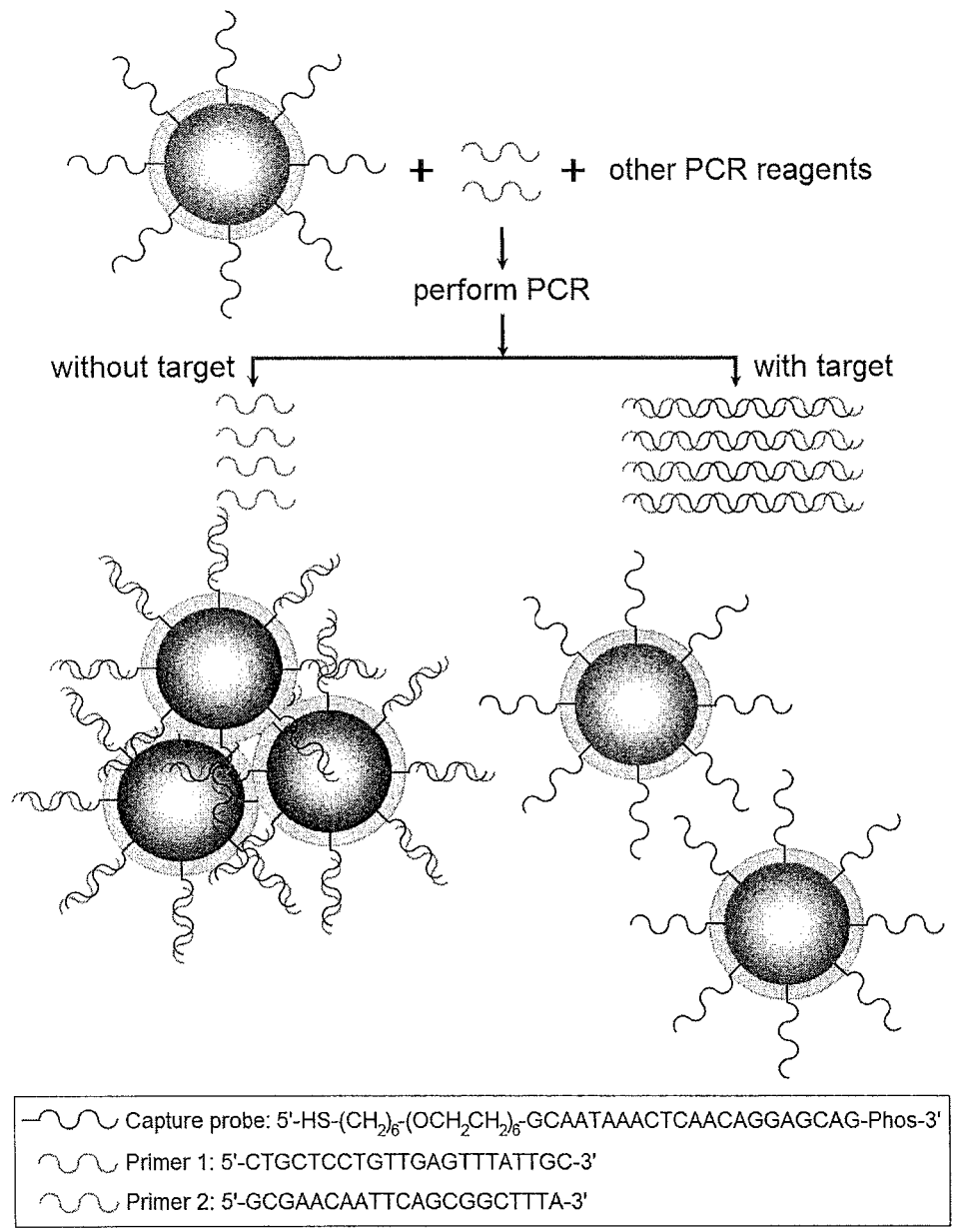
FIG. 11 presents a schematic illustration of the closed-tube colorimetric PCR detection platform. Depicted are sequences for Capture probe (SEQ ID NO.: 2), Primer 1 (SEQ ID NO:3), and Primer 2 (SEQ ID NO: 4).

Taking advantage of the thermal stability, hybridization-induced color change property, as well as PCR compatibility of the silica-modified oligonucleotide-AuNP conjugate, a closed-tube colorimetric PCR detection platform is developed (FIG. 11). The reaction mixture is almost identical to the standard ones except the additional silica-modified oligonucleotide-AuNP conjugate and slightly higher MgCl$_2$ concentration. In the absence of the target (i.e., φX174), Primer 1 remains intact after PCR and hybridizes with the AuNP-bound sequence, thereby leading to particle aggregation and the solution color turning purple. The other primer (Primer 2), being non-complementary to the AuNP-bound sequence, would not contribute to or affect the solution color change. In the presence of the target, both primers are extended and give rise to double-stranded amplicon (151 base pairs long). Hence, Primer 1 is no longer available to trigger the aggregation and the solution remains red. As expected, the proof-of-concept results of the closed-tube colorimetric PCR detection platform were purple and red in color for the negative and positive samples, respectively (FIG. 10B, samples 9 and 10). Indeed, both samples were red in color right at the end of PCR and the photograph presented here was taken 40 min afterward. The color difference was also monitored by UV-vis spectrophotometry. Particle aggregation in the negative sample experienced a slight red shift in the SPR absorption peak from ~520 nm to ~530 nm, with a concomitant decrease in absorbance at 520 nm and increase in absorbance at 650 nm (FIG. 10C).

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A conjugate comprising:
   (i) a nanoparticle having an outer surface;
   (ii) a silica layer coated on said outer surface of said nanoparticle; and
   (iii) a plurality of macromolecules attached directly to said outer surface of said nanoparticle via a linkage group;
   wherein said linkage group resides within said silica layer;
   wherein said plurality of macromolecules comprises members selected from the group consisting of an oligonucleotide, an aptamer, a small interfering RNA, a peptide, a protein, an antibody, and polyethylene glycol; and
   wherein said members are exposed and functionally accessible;
   wherein said nanoparticle is a gold nanoparticle (AuNP) or a silver nanoparticle (AgNP);
   wherein said silica layer is formed with 3-mercaptopropyltrimethoxysilane (MPTMS);
   wherein after hydrolysis and polycondensation of trimethoxysilyl groups of said MPTMS a single or a few silica monolayers are formed; and
   wherein said linkage group displays greater thermal and chemical stability when compared to the same linkage group in a conjugate without said silica layer.

2. The conjugate of claim 1, wherein said nanoparticle is a gold nanoparticle (AuNP).

3. The conjugate of claim 1, wherein said member of the plurality of macromolecules is an oligonucleotide.

4. The conjugate of claim 1, wherein said member of the plurality of macromolecules is an aptamer.

5. The conjugate of claim 1, wherein member of the plurality of macromolecules is a small interfering RNA.

6. An assay system, comprising
   (i) an enzyme; and
   (ii) said conjugate of claim 1.

7. The assay system of claim 6, further comprising
   (iii) a DNA primer,
   wherein said enzyme is Taq DNA polymerase,
   wherein said conjugate is an oligonucleotide-AuNP conjugate comprising an oligonucleotide, and
   wherein said DNA primer has a nucleotide sequence complementary to said oligonucleotide of said oligonucleotide-AuNP conjugate.

8. The assay system of claim 6, further comprising
   (iii) a DNA primer,
   wherein said enzyme is Taq DNA polymerase,
   wherein said conjugate is an oligonucleotide-AgNP conjugate comprising an oligonucleotide, and
   wherein said DNA primer has a nucleotide sequence complementary to said oligonucleotide of said oligonucleotide-AgNP conjugate.

9. A therapeutic agent carrier comprising a therapeutic agent and the conjugate of claim 1.

10. The therapeutic agent carrier of claim 9, wherein said conjugate is an oligonucleotide-AuNP conjugate and wherein said therapeutic agent is connected or linked to said AuNP of said oligonucleotide-AuNP conjugate, to said oligonucleotide of said oligonucleotide-AuNP conjugate or to a sequence complementary to said oligonucleotide-AuNP conjugate.

11. The therapeutic agent carrier of claim 9, wherein said conjugate is an oligonucleotide-nanoparticle and wherein said therapeutic agent carrier is connected or linked to said oligonucleotide-nanoparticle.

12. The conjugate of claim 1, wherein said member of the plurality of macromolecules is an antibody.

13. The conjugate of claim 1, wherein said linkage group is selected from the group consisting of a thiol linkage, an amino linkage, a diol linkage and a carboxyl linkage.

14. The conjugate of claim 1, wherein said member of the plurality of macromolecules is a peptide or protein.

15. The conjugate of claim 1, wherein said member of the plurality of macromolecules is a synthetic polymer.

16. The conjugate of claim 3, wherein said oligonucleotide is chemisorbed onto said surface of said nanoparticle via a thiol linkage attached to said oligonucleotide.

17. The assay system of claim 6, wherein said member of the plurality of macromolecules is selected from the group consisting of an aptamer, a peptide, a protein, an antibody a small RNA, and a synthetic polymer.

18. The assay system of claim 6, wherein said member of the plurality of macromolecules is an oligonucleotide.

19. The assay system of claim 6, wherein said nanoparticle is a gold nanoparticle (AuNP).

20. The assay system of claim 18, wherein said oligonucleotide comprises a fluorescent label.

21. A method for detecting a nucleic acid, said method comprising the steps of:
  (a) hybridizing a target nucleic acid to said conjugate of claim 1, wherein said member of the plurality of macromolecules is an oligonucleotide complementary to said target nucleic acid; and
  (b) detecting said target nucleic acid.

22. A method for amplifying a nucleic acid, said method comprising the steps of:
  (a) hybridizing a target nucleic acid to said conjugate of claim 1, wherein said member of the plurality of macromolecules is an oligonucleotide complementary to said target nucleic acid; and
  (b) amplifying said target nucleic acid.

23. A closed-tube colorimetric polymerase chain reaction method, said method comprising the step of:
  (a) adding said conjugate of claim 1 to a sample comprising a target nucleic acid, wherein said member of the plurality of macromolecules is an oligonucleotide complementary to said target nucleic acid.

24. The method of claim 23, further comprising the step of:
  (b) monitoring a color difference in said sample by UV-vis spectrophotometry.

* * * * *